(12) United States Patent
Morimoto et al.

(10) Patent No.: US 10,610,420 B2
(45) Date of Patent: *Apr. 7, 2020

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Kaoru Ishihara, West Chester, OH (US); Sarah Marie Wade, Springfield Township, OH (US); LeAnn Nichole Phillips, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

This patent is subject to a terminal disclaimer.

(21) Appl. No.: 15/632,447

(22) Filed: Jun. 26, 2017

(65) Prior Publication Data

US 2017/0290716 A1    Oct. 12, 2017

Related U.S. Application Data

(63) Continuation of application No. PCT/CN2014/094890, filed on Dec. 25, 2014.

(51) Int. Cl.
*A61F 13/15* (2006.01)
*A61F 13/20* (2006.01)
(Continued)

(52) U.S. Cl.
CPC ...... *A61F 13/49011* (2013.01); *A61F 13/496* (2013.01); *A61F 13/64* (2013.01); *A61F 13/49* (2013.01)

(58) Field of Classification Search
CPC .......... A61F 13/15585; A61F 13/49001; A61F 13/49011; A61F 13/49014;
(Continued)

(56) References Cited

U.S. PATENT DOCUMENTS

| | | |
|---|---|---|
| 2,462,195 A | 2/1949 | Jacobson |
| 2,513,039 A | 6/1950 | Miller |

(Continued)

FOREIGN PATENT DOCUMENTS

| | | |
|---|---|---|
| CN | 2167695 | 8/1994 |
| CN | 1246324 | 8/2000 |

(Continued)

OTHER PUBLICATIONS

All Office Actions, U.S. Appl. No. 15/632,454.
(Continued)

*Primary Examiner* — Michele M Kidwell
(74) *Attorney, Agent, or Firm* — Richard L. Alexander (57) ABSTRACT

Disclosed is a wearable article 20 comprising a main body 38 and a ring-like elastic belt 40 comprising a front belt 84 and a back belt 86 formed by a plurality of elastic bodies, at least some of the elastic bodies removed of its elasticity by an elastic cut window; the front and back belt each having a set of elastic cut windows, the transverse width of the elastic body having the longest length removed of its elasticity defined as a maximum elastic cut window 24W; wherein the maximum elastic cut window of the back belt is greater than the maximum elastic cut window of the front belt.

19 Claims, 9 Drawing Sheets

(51) Int. Cl.
*A61F 13/49* (2006.01)
*A61F 13/496* (2006.01)
*A61F 13/64* (2006.01)

(58) Field of Classification Search
CPC ............ A61F 13/49017; A61F 13/4902; A61F 13/496; A61F 13/5622; A61F 13/64; A61F 2013/49025; A61F 2013/49088
See application file for complete search history.

(56) References Cited

U.S. PATENT DOCUMENTS

| | | | |
|---|---|---|---|
| 2,632,177 | A | 3/1953 | Bigger |
| 3,080,869 | A | 3/1963 | Alberts |
| 3,824,812 | A | 7/1974 | Matthews et al. |
| D281,540 | S | 12/1985 | Ternstrom |
| 5,787,512 | A | 8/1998 | Knox |
| 7,901,393 | B2 | 3/2011 | Matsuda et al. |
| 8,206,365 | B2 | 6/2012 | Norrby |
| 8,382,735 | B2 | 2/2013 | Torigoshi et al. |
| 8,518,008 | B2 | 8/2013 | Toshiyasu et al. |
| 8,518,009 | B2 | 8/2013 | Saito et al. |
| 8,555,419 | B2 | 10/2013 | Demarest et al. |
| 9,011,404 | B2 | 4/2015 | Kobayashi et al. |
| 9,023,006 | B2 | 5/2015 | Shunsuke et al. |
| 9,023,007 | B2 | 5/2015 | Hashino et al. |
| 9,358,162 | B2 | 6/2016 | Kuwano et al. |
| 9,592,163 | B2 | 3/2017 | Morimoto et al. |
| 9,827,149 | B2 | 11/2017 | LaVon et al. |
| 10,064,763 | B2 | 9/2018 | Takahashi et al. |
| 2005/0107763 | A1 | 5/2005 | Matsuda et al. |
| 2007/0208317 | A1 | 9/2007 | Krautkramer et al. |
| 2009/0118689 | A1 | 5/2009 | Lawson et al. |
| 2010/0286646 | A1 | 11/2010 | Takino et al. |
| 2011/0184372 | A1* | 7/2011 | Esping Ostlin ... A61F 13/49012 604/392 |
| 2011/0251576 | A1 | 10/2011 | Ando et al. |
| 2013/0079742 | A1 | 3/2013 | Kuwano et al. |
| 2013/0138072 | A1 | 5/2013 | Morimoto et al. |
| 2013/0211363 | A1 | 8/2013 | LaVon et al. |
| 2013/0310795 | A1 | 11/2013 | Glahn et al. |
| 2013/0338623 | A1 | 12/2013 | Kinoshita et al. |
| 2014/0358110 | A1 | 12/2014 | Takahashi et al. |
| 2016/0184145 | A1* | 6/2016 | Morimoto ......... A61F 13/49011 604/385.29 |
| 2017/0290711 | A1* | 10/2017 | Morimoto ......... A61F 13/49011 |
| 2017/0290721 | A1* | 10/2017 | Morimoto ......... A61F 13/49011 |
| 2018/0200122 | A1 | 7/2018 | Maki |
| 2018/0333311 | A1 | 11/2018 | Maki |
| 2018/0369027 | A1 | 12/2018 | Fukasawa |

FOREIGN PATENT DOCUMENTS

| | | |
|---|---|---|
| EP | 2659870 | 11/2013 |
| JP | H0871107 | 3/1996 |
| JP | H9271488 | 10/1997 |
| JP | 2001212176 | 8/2001 |
| JP | 2007029479 | 2/2007 |
| JP | 2009125087 | 6/2009 |
| JP | 2012095937 | 5/2012 |
| JP | 2012135519 | 7/2012 |
| JP | 2013013580 | 1/2013 |
| JP | 2013255561 A | 12/2013 |
| JP | 2013255570 A | 12/2013 |
| JP | 5566550 | 8/2014 |
| JP | 2014147506 | 8/2014 |
| JP | 2014150909 | 8/2014 |
| JP | 2018064698 A | 4/2018 |
| JP | 2018138272 A | 9/2018 |
| WO | WO-0185080 | 11/2001 |
| WO | WO-2007144838 | 12/2007 |
| WO | WO-2009031592 | 3/2009 |
| WO | 2009119195 | 10/2009 |
| WO | WO2015108091 A1 | 7/2015 |
| WO | WO2016029655 | 3/2016 |
| WO | WO2016103873 A1 | 6/2016 |
| WO | WO2018159093 A1 | 9/2018 |

OTHER PUBLICATIONS

International Search Report and Written Opinion, PCT/CN2014/094890, dated Sep. 21, 2015.

Supplemental International Search Report and Written Opinion, PCT/CN2014/094890, dated Feb. 23, 2017.

\* cited by examiner

WEARABLE ARTICLE HAVING ELASTIC BELT

CROSS REFERENCE TO RELATED APPLICATIONS

This application is a continuation, under 35 USC 120, of Application No. PCT/CN2014/094890, filed on Dec. 25, 2014, which is herein incorporated by reference in its entirety.

FIELD OF THE INVENTION

The present invention relates to wearable articles having an elastic belt having profiled elastic cut windows.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tend to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. On the other hand, certain pant-type wearable articles are configured such that the outer cover of the wearable body completely covers the entirety of the garment-facing surface of the article. Such pant-type wearable articles may be referred to as uni-body pants. Belt-type pants, compared to uni-body pants, may be advantageous in having better breathability by having less layers of material in certain areas of the articles, and in that they may be manufactured economically.

There is a desire to provide belt-type wearable articles to have balanced or improved performance without compromising the cost effectiveness of a belt-type wearable article. For example, there is desire to provide wearable articles to better fit the human body, particularly to a lower torso of a child of less than 36 months of age. Compared to that of an adult, the young child has a relatively bigger front belly and protruding buttock. In another example, there is desire to provide wearable articles having an absorbent body to have closer contact with the genital area to provide better containment capacity and prevent leakage.

Based on the foregoing, there is a need for a pant-type wearable article having balanced performance such as fit, coverage of buttock area, comfort during wear, prevention of sagging, and prevention of leakage. There is further a need for providing such a wearable article in an economical manner.

SUMMARY OF THE INVENTION

The present invention is directed to a wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other, and at least a portion of the elasticity of at least some of the elastic bodies are removed of its elasticity, the transverse width of the elastic body removed of its elasticity defined as an elastic cut window;

the front belt having a set of elastic cut windows, the transverse width of the elastic body having the longest length removed of its elasticity defined as a maximum elastic cut window of the front belt;

the back belt having a set of elastic cut windows, the transverse width of the elastic body having the longest length removed of its elasticity defined as a maximum elastic cut window of the back belt;

wherein the maximum elastic cut window of the back belt is greater than the maximum elastic cut window of the front belt.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 1:
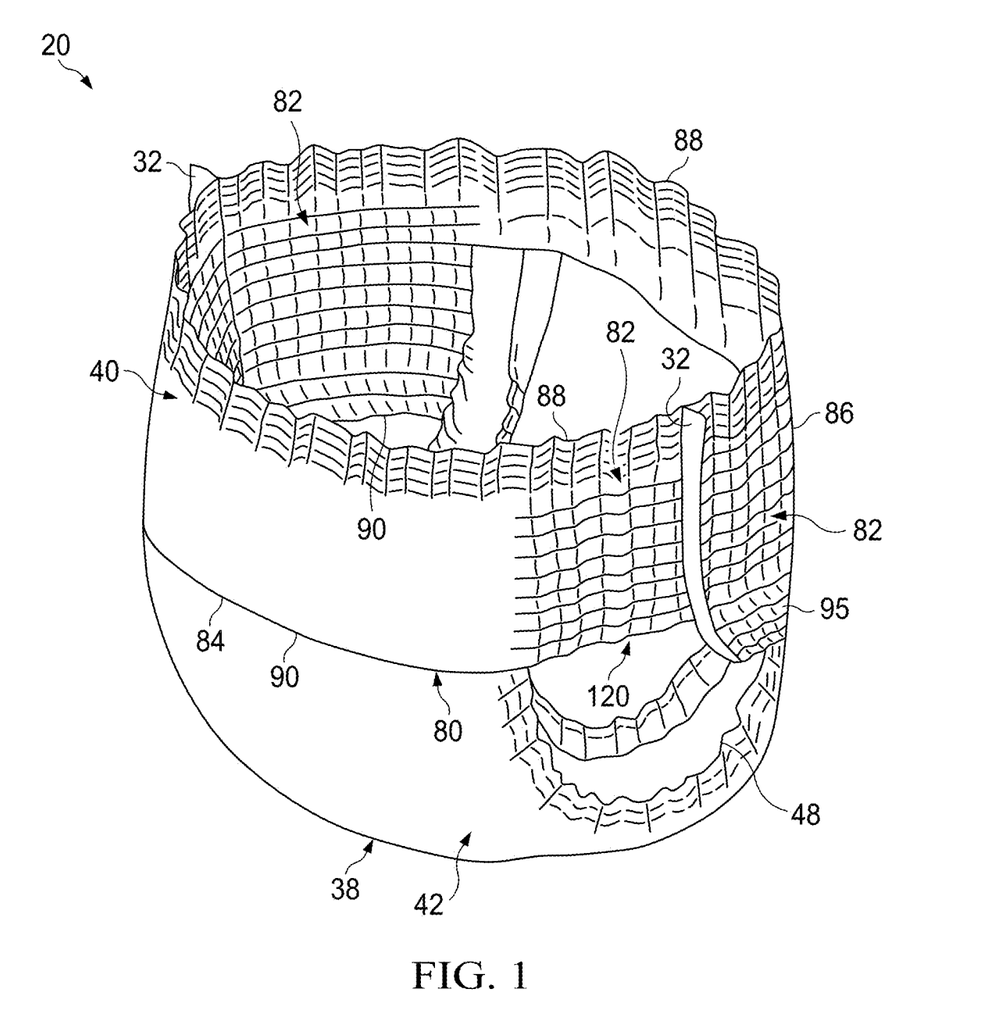
FIG. 1 is a perspective view of one embodiment of a wearable article of the present invention.
Figure 2:
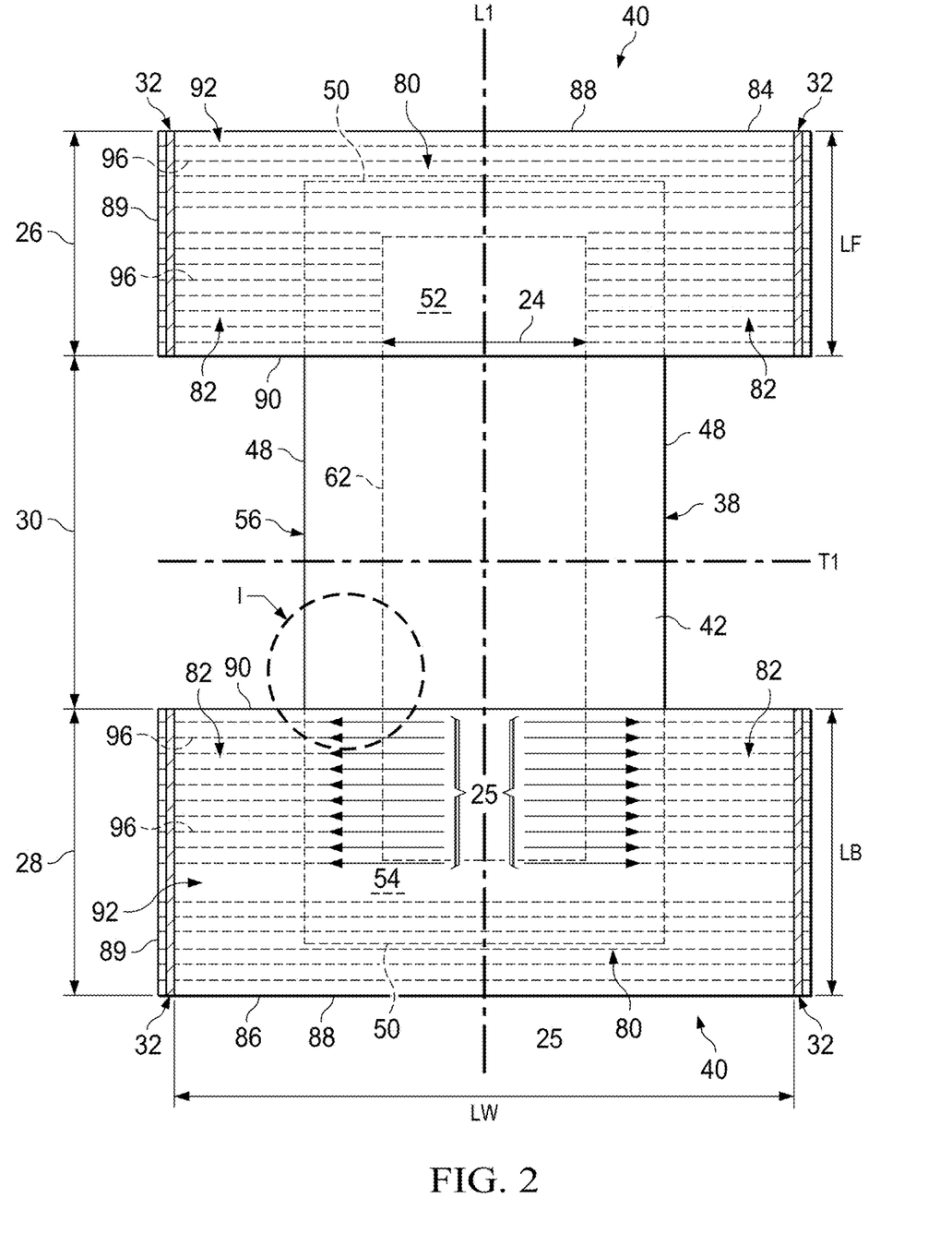
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap.

The main body may comprise a liquid pervious topsheet, a liquid impervious backsheet, and the absorbent core 62 encased between the topsheet and the backsheet. The absorbent core 62 may include an acquisition/distribution layer and a storage layer 63.

The absorbent core 62 may comprise any absorbent material that is generally compressible, conformable, non-irritating to the wearer's skin, and capable of absorbing and retaining liquids such as urine and other certain body exudates, such as superabsorbent particulate polymer material, comminuted wood pulp, which is generally referred to as airfelt, creped cellulose wadding, melt blown polymers, including co-form, chemically stiffened, modified or crosslinked cellulosic fibers, tissue, including tissue wraps and tissue laminates, absorbent foams, absorbent sponges, or any other known absorbent material or combinations of materials.

Figure 3:
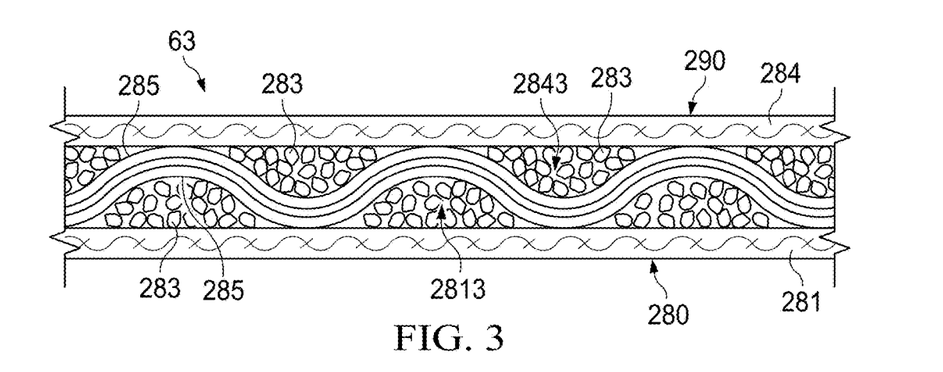
FIG. 3 is a schematic cross section view of an absorbent core suitable in one embodiment of the present invention.

The amount of absorbent particulate polymer material present in the absorbent core 62 may vary, but in certain embodiments, is present in the absorbent core 62 in an amount greater than 80% by weight of the absorbent core, or greater than 85% by weight of the absorbent core, or greater than 90% by weight of the absorbent core, or greater than 95% by weight of the core. In a particular embodiment, the absorbent core 62 consists essentially of a first and second substrates 281, 284, the absorbent particulate polymer material 283, and a thermoplastic adhesive material 285. In an embodiment, the absorbent core 62 may be substantially cellulose free. Such substantially cellulose free absorbent core 62 is useful in that the main body 38 may be made with low caliper, which may be comfortable for the wearer, appealing to the wearer as being undergarment-like, and cost effective in view of transportation and storage.

Referring to FIG. 3, the storage layer 63 may include a first and second absorbent layers 280, 290, the first absorbent layer 280 including a first substrate 281 and the second absorbent layer 290 including a second substrate 284, the first and second absorbent layers 280, 290 further including superabsorbent particulate polymer material 283 deposited on said first and second substrates 281, 284 and thermoplastic adhesive material 285 covering the absorbent particulate polymer material 283 on the respective first and second substrates 281, 284, said first and second absorbent layers 280, 290 combined together such that at least a portion of said thermoplastic adhesive material 283 of said first absorbent layer 280 contacts at least a portion of the thermoplastic adhesive material 285 of said second absorbent layer 290, the absorbent particulate polymer material 283 is disposed between the first and second substrates 281, 284 in an absorbent particulate polymer material area, and the absorbent particulate polymer material 283 is substantially continuously distributed across the absorbent particulate polymer material area. The absorbent particulate polymer material 283 may be deposited on the first and second substrates 281, 284 in respective patterns of land areas 2813 and junction areas 2843 between the land areas 2813 such that the absorbent particulate polymer material 283 is discontinuously distributed on the first and second substrates 281, 284; and the first and second absorbent layers 281, 284 are combined together such that the respective patterns of absorbent particulate polymer material 283 are offset from one another.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.) herein incorporated by reference.

Referring to FIGS. 1 and 2, the ring-like elastic belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, the front belt 84 and back belt 86 may each comprise an inner sheet 94, an outer sheet 92, (hereinafter also collectively "belt sheets") and a plurality of elastic bodies 96 sandwiched therebetween and running in the transverse direction substantially parallel to each other, and configured to impart elasticity per each zone according to the relationship described below. (The inner sheet 94 is not shown.) Such an article may be economically made.

In one embodiment, the transverse width LW of the back belt 86 in the uncontracted condition may be the same as the transverse width of the front belt 84 of the same condition. In one embodiment, each of the proximal edges 90 and the distal edges 88 of the front belt 84 and the back belt 86 may be substantially parallel, as in FIG. 2.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1-2). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1. In such embodiment, the proximal portion of the back belt beyond the proximal edge of the front belt is defined as a buttock cover zone 110, as in FIG. 4.

Figure 4:
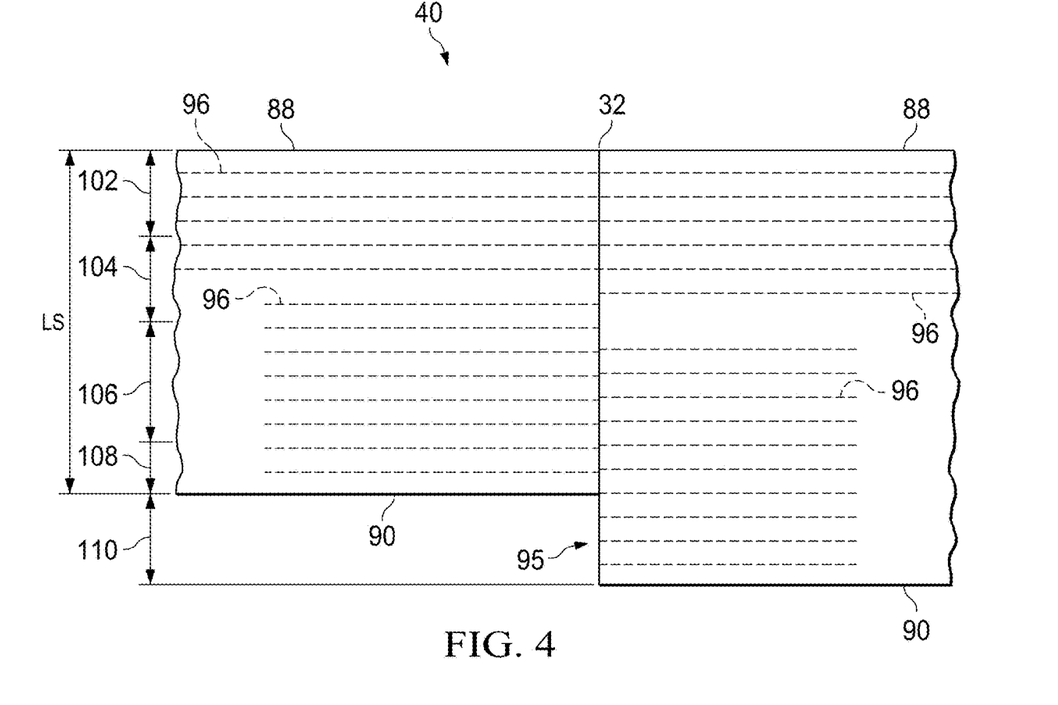
FIG. 4 is a schematic side plan view of one embodiment of a wearable article of the present invention in a flat uncontracted condition showing the garment facing surface.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS, as in FIG. 4. When the front belt 84 has straight distal edges 88 and proximal edges 90 that are substantially parallel of each other, then the longitudinal length LF of the front belt 84 is equal to the seam length LS.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. In one embodiment, the front and back belts 84, 86 may be provided in non-woven material having a basis weight of less than 45 gsm for sake of breathability perception and softness of the belt 40.

The tensile stress (N/m) of the front and back elastic belts 84, 86, respectively, may be profiled in order to provide the benefits of the present invention. The tensile stress may be measured, for example, by the Belt Zone Tensile Stress Measurement described herein below. The waist belt 40 exhibits elasticity due to the plurality of elastic bodies 96 running in the transverse direction, wherein the elastic bodies 96 adhered to the inner and outer sheets 92, 94 impart elasticity to the waist belt 40. Tensile stress of the waist belt 40 may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body 96. Each elastic body 96 disposed on the waist belt 40 may be disposed over the entire transverse width LW. Some elastic bodies 96 may be removed of its elasticity contributing to the elasticity of the waist belt 40 in the transverse center of the front and/or back belt 84, 86. When a portion of an elastic body is not contributing to the elasticity of the waist belt 40, the remainder of the intact elastic body capable of imparting elasticity to the waist belt 40 is defined as the "effective length of elasticity of an elastic body". An elastic body unadhered to the inner and outer sheets 92, 94 may be left dangling, thereby still exhibiting elasticity as an elastic body per se. However, so long as the elasticity is non-contributory to elasticity of the waist belt 40, such length or area is described herein as "non-elastic".

In the present invention, the elasticity of the elastic body 96 may be removed by the steps of:
  (a) advancing the inner and outer sheets 92 94, in a machine direction;
  (b) advancing and stretching the elastic body 96 in the machine direction;
  (c) adhering the elastic body 96 between the inner and outer sheets 92, 94 wherein at least a certain portion of the elastic body is left unadhered, the unadhered portion being an elastic cut window 24; and
  (d) cutting the elastic body at the elastic cut window 24.

As such, the transverse width of the elastic cut window 24 defines the length for which the elasticity of the elastic body 96 is removed. The front or back belt 84, 86 may comprise a plurality of elastic bodies 96 having an elastic cut window 24. The accumulative elastic cut windows for a front belt 84 or a back belt 86 is herein defined as a set of elastic cut windows 25. The accumulative area wherein the set of elastic cut windows 25 exist may create a non-elastic region for the front or back belt 84, 86. There may exist a set of elastic cut windows 25 per one front belt 84 or per one back belt 86. For each set of elastic cut windows 25, the transverse width may be consistent to provide more or less a rectangular non-elastic region, or the transverse width of the elastic cut windows 24 may be varied. When the elastic cut windows 24 within a set of elastic cut windows 25 has a varied transverse width such as in FIGS. 6-9, the widest elastic cut window is defined as a maximum elastic cut window 24W.

In addition to utilizing methods such as variation of elongation rate of the elastic body, density (dtex) of the elastic body, the longitudinal interval of multiple elastic bodies, or any combination of such methods, the article of the present invention utilizes a variation of elastic cut windows for effectively adjusting the tensile stress of a certain area or zone within the front and/or back belt 84, 86. The article of the present invention may have sets of elastic cut windows 25 that are different in maximum elastic cut window 24W, or have different sets of elastic cut windows 25 between the front and back belt 84, 86, or have varied elastic cut windows 24 within the front belt or back belt 84, 86, for providing good fit to the wearer. The method of utilizing elastic cut windows 24 for adjusting the tensile stress of the elastic belt is advantageous in that such adjustment may be effected by simply changing the unadhered length of the elastic bodies to be cut, which does not add significant cost for manufacturing the article.

The article of the present invention may be configured such that the maximum elastic cut window 24W of the back belt is greater than the maximum elastic cut window 24W of the front belt, as in FIG. 2. Not all of the elastic cut windows of the back belt 86 need be greater than the elastic windows of the front belt 84. The article of the present invention may have at least one of the front belt or the back belt, or both of the front belt and back belt, comprising varied elastic cut windows within the set of elastic cut windows 25, such as in FIGS. 6-9. Such profiling of the elastic cut window may accommodate the proportionately large belly and large buttock of a young child. The profiling is described in more detail with reference to zones created by the front and back belt.

Referring to FIG. 4, the front and back belts 84, 86 are each divided into at least 4 zones extending in the transverse direction and defined of its position from the distal edge 88 to the proximal edge 90 relative to the percentage of the seam length LS. The entirety of the length of the belt side edge 89 of the front belt 84 is seamed with a certain length of the belt side edge 89 of the back belt 86 to define a seam length LS. When seam length LS is considered 0% at the distal edge 88 and 100% at the proximal edge 90 of the front belt 84, the zones are defined as such: 0-25% is the waist zone 102, 25-50% is the distal tummy zone 104, 50-85% is the proximal tummy zone 106, and 85-100% is the leg zone 108. For embodiments where the back belt 86 has a greater longitudinal length LB than the longitudinal length LF of the front belt 84, the remaining length of "LB minus LS" of the back belt 86 is not counted in the 4 zones described above. For such embodiment, the proximal portion of the back belt beyond the proximal edge of the front belt is defined as buttock cover zone 110. When there is an elastic body disposed at 25% from the distal edge 88, such elastic body is considered to be included in the waist zone 102. When there is an elastic body disposed at 50% from the distal edge 88, or 85% from the distal edge 88, such elastic body is considered to be included in the proximal tummy zone 106. When there is an elastic body disposed at 100% from the distal edge 88, such elastic body is considered to be included in the buttock cover zone 110.

Referring to FIGS. 2 and 6-9, the elastic cut windows 24 may be disposed to provide a non-elastic region in an area where the waist belt 40 overlaps the front and/or back waist panel 52, 54 when the main body 38 comprises an absorbent core 62. Such a configuration is advantageous in that this may alleviate the elasticity of the waist belt 40 causing bunching of the absorbent core 62, which may cause interference with close fit of the main body 38 to the wearer. The overlapping area of the elastic cut windows 24 and absorbent core 62 may be adjusted so that containment capability of the absorbent core 62 and good fit of the waist belt 40 are both achieved. The overlapping area of the elastic windows 24 and absorbent core 62 may be adjusted for providing size variation.

Figure 5:
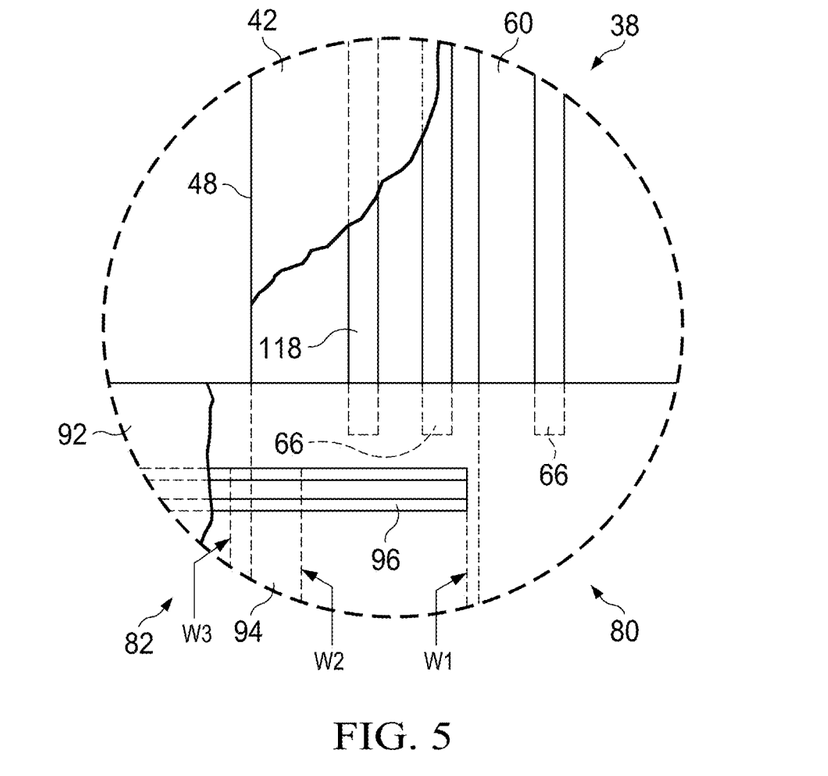
FIG. 5 is an exploded plan view of one embodiment of the present invention taken along area I of FIG. 2.

Referring to FIGS. 2 and 5, the elastic cut windows 24 of the back belt toward the proximal edge 90 may be the maximum elastic cut window 24W, and may have a certain lateral distance in relation to the absorbent core 62 or the main body 38. As described above, the width of the elastic cut window 24 may be wider than the absorbent core 62, namely the effective length of elasticity of the belt elastic 96 ending at line W1. The main body 38 herein may comprise a pair of cuffs disposed along and extending from the longitudinal side edges of the main body, each cuff comprising an outmost leg elastic body 118 at the distal edge of the cuff. In one embodiment, the width of the maximum elastic cut window 24W of the back belt may be greater than the lateral distance between the outmost leg elastic bodies 118, namely the effective length of elasticity of the belt elastic 96 ending at line W2. The main body 38 may be disposed of more than one cuff elastic bodies 66 on each side. In one embodiment, the width of the maximum elastic cut window 24W of the back belt may be greater than the lateral distance of the main body 38, namely the effective length of elasticity of the belt elastic 96 ending at line W3. By providing the maximum elastic cut window 24W of the back belt greater than the lateral distance between the outmost leg elastic bodies 118, or even greater than the lateral distance of the main body 38, the elastic bodies 96 of the back belt interfere less with the outmost leg elastic bodies 118, which allows the back waist panel 54 to fit closely to the wearer. Such a configuration may be particularly advantageous for articles having an absorbent core 62 with low caliper, such as those described above. In one embodiment, the maximum elastic cut window 24W of the back belt 86 is disposed on the buttock cover zone 110.

In another embodiment, profiling of the elastic cut windows 24 of the waist belt 40 may accommodate the proportionately large belly and large buttock of a young child. Referring to FIGS. 6-9, the back belt 86 may comprise elastic cut windows 24 in at least the proximal tummy zone 106 and the leg zone 108, and the elastic cut windows 24 of the leg zone 108 may be greater than the elastic cut windows of the proximal tummy zone 106. The back belt 86 may further comprise elastic cut windows 24 in the distal tummy zone 104, and the elastic cut windows 24 of the proximal tummy zone 106 are greater than the elastic cut windows 24 of the distal tummy zone 104. In one embodiment, the tensile stress of the back belt may be in a relationship of: distal tummy zone>proximal tummy zone>leg zone.

Figure 6:
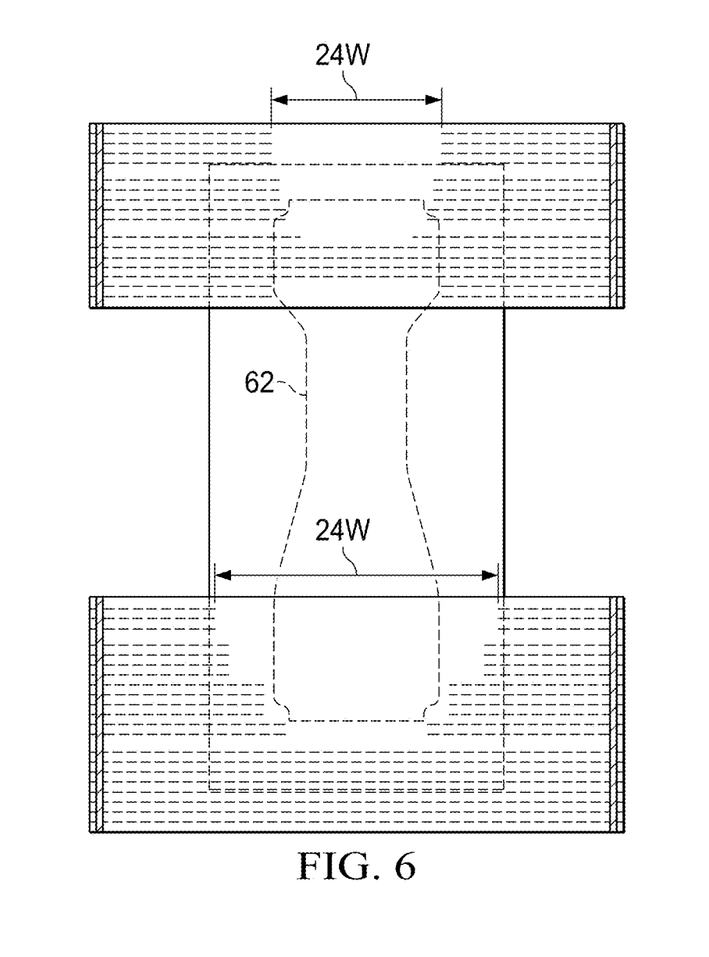
FIG. 6 is a schematic plan view of one embodiment of a wearable article of the present invention with the seams unjoined and in a flat uncontracted condition showing the garment facing surface.
Figure 7:
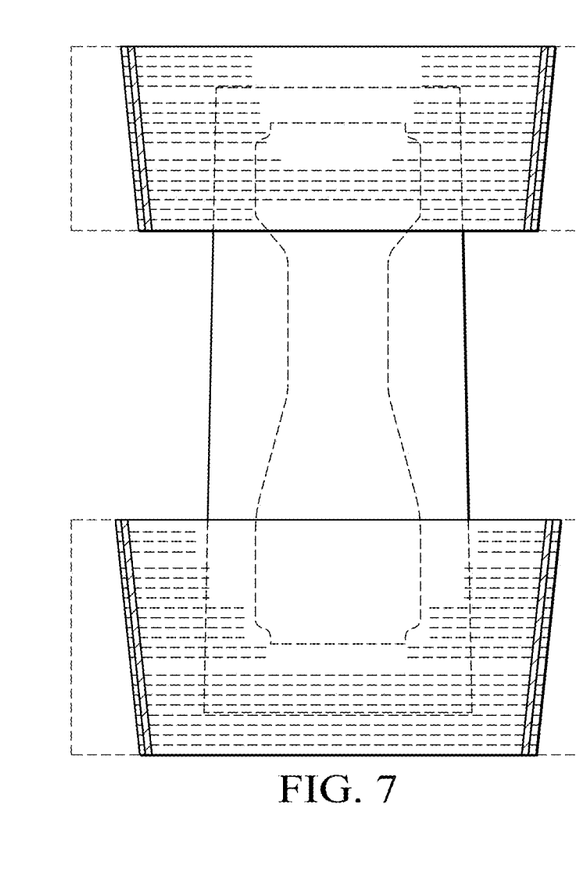
FIG. 7 is a schematic plan view of FIG. 6 in a contracted condition.
Figure 8:
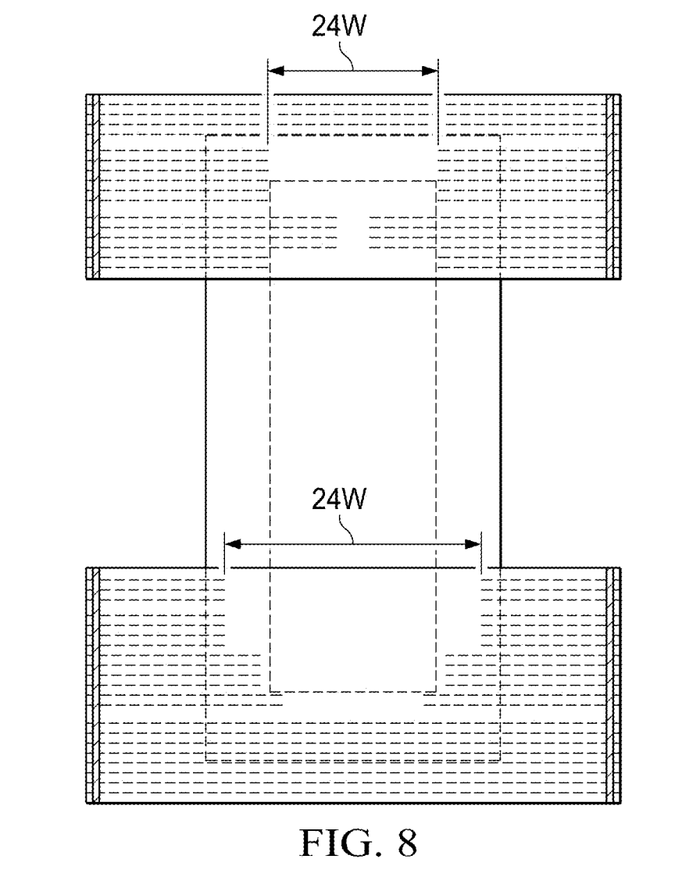
FIGS. 8-9 are schematic plan views of embodiments of a wearable article of the present invention with the seams unjoined and in a flat uncontracted condition showing the garment facing surface.
Figure 9:
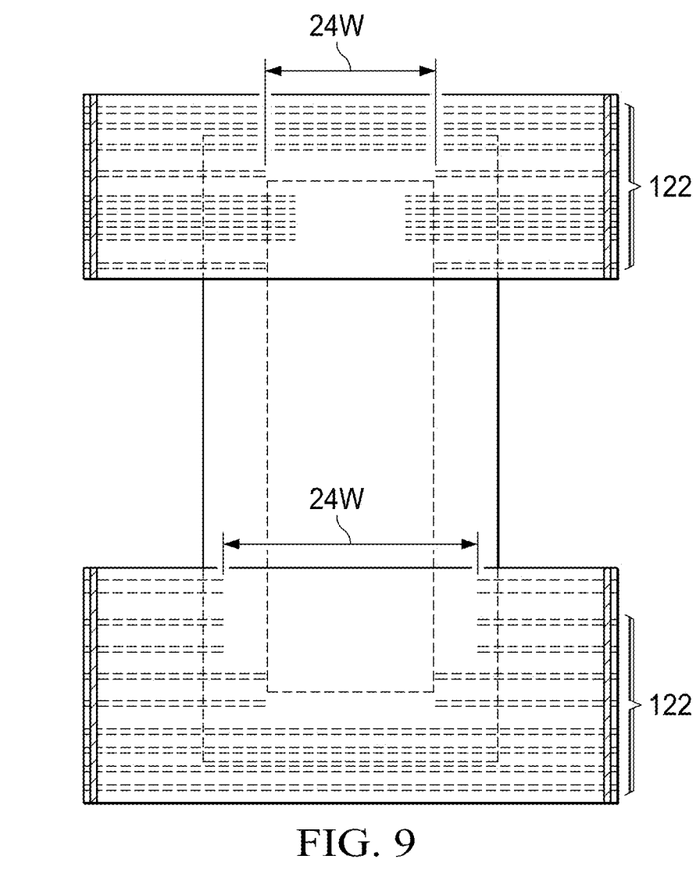

In the present article, the maximum elastic cut window 24W of the front belt may be disposed on the distal tummy zone 104 or the leg zone 108. Referring to FIG. 8-9, the elastic cut windows 24 of the elastic bodies disposed on the front proximal tummy zone 106 may be smaller than the elastic cut windows 24 of the elastic bodies disposed on the front distal tummy zone 104 and the front leg zone 108. Referring to FIG. 6-7, there may be no elastic cut windows 24 disposed on the front proximal tummy zone 106.

Without being bound by theory, such profiling of the tensile stress per zone for embodiments of FIGS. 6-9 is believed to provide the article of the present invention with a shaped elastic belt 40 that conforms well to a human body, particularly to a lower torso of a child of less than 36 months of age, and therefore provides good fit and comfort to the wearer, without compromise of sagging prevention or leakage prevention. Namely, the front proximal tummy zone 106 is subject to high tensile stress such that the article may be anchored against the wearer's trochanter, while leaving more area for the back proximal tummy zone 106 to accommodate the wearer's buttock. As long as the article is anchored securely at the trochanter, the leg zone 108 adjacent the front leg opening region 120 may be provided with significantly lower tensile stress compared to the proximal tummy zone 106. Thus, the soft fit at the front leg opening region 120 facilitates leg movement. Further, by providing a higher tensile stress to the back distal tummy zone 104 compared to the front distal tummy zone 104, the wearer's front waist area is accommodated.

Figure 10:
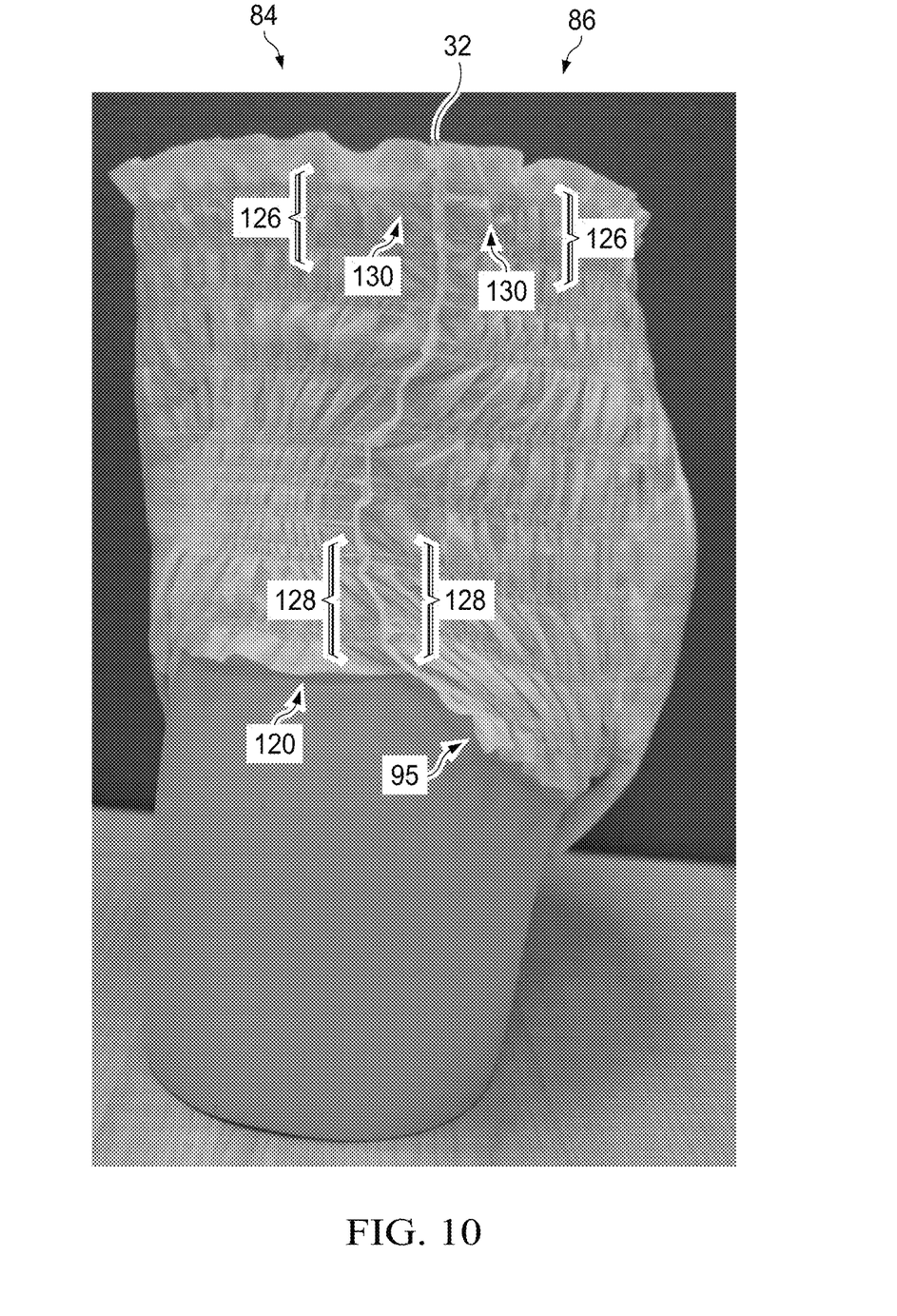
FIG. 10 is a side view of one embodiment of a wearable article of the present invention worn on a mannequin.

FIG. 6 is a schematic plan view of one embodiment of a wearable article of the present invention with the seams unjoined and in a flat uncontracted condition showing the garment facing surface, whereas FIG. 7 is the same embodiment in a contracted condition. Referring to FIGS. 6 and 7, by providing the tensile stress per zone of the front and back elastic belts by way of profiling the elastic cut windows 24, the front belt 84 may be configured to provide higher tensile stress toward the distal edge than the proximal edge to accommodate the wearer's front belly while anchoring the belt at the front proximal tummy zone 106, while the back belt 86 may be configured to provide higher tensile stress toward the proximal edge than the distal edge to accommodate the wearer's back buttock. Such shaped elastic belt 40 may provide the article to take an S-curve side seam 32 observed by the side when worn by the wearer, such as shown in FIG. 10.

FIG. 9 is a schematic plan view of one embodiment of a wearable article of the present invention wherein the elastic bodies 96 of the belt 40 of the present invention are arranged in arrays 122. The arrays of the present invention, have at least 2 elastic bodies 96 disposed in close proximity to each other in the longitudinal direction. Specifically, a plurality of elastic bodies 96 are disposed at an interval of 2-4 mm. Without being bound by theory, by disposing the elastic bodies 96 in such close proximity to each other, the array exhibits a behavior as if it were one elastic body with a certain width, and provides various benefits. For example, the array provides more or less the combined tensile force of the elastic bodies 96 in the array, such that each elastic body 96 may be disposed at a much lower tensile force. Further, the gathers created in the interval of the array are so fine that the area of the inner sheet 94 facing the wearer is significantly increased. Such increased area of material in the interval, combined with the elastic bodies 96 of the array, apply a tensile force to the wearer over a distributed width, compared to the width of a single elastic body. Namely, the array exhibits a behavior as if it were one elastic body. As such, the array may provide a good fit to the wearer by using relatively low density elastic bodies which are economically supplied. The reduction of tensile force in a concentrated area compared to that of a single elastic body, may also reduce red marking on the skin of the wearer, and provide the wearer with a more comfortable and soft fit. Further, an array may provide the appearance of an elastic body of a certain width, similar to elastic bodies disposed on a durable undergarment. Thus, disposal of an array may connote an undergarment look, or high quality. For example, referring to FIG. 10, a waist band appearance 126 or a leg band appearance 128 may be provided. Further, a finger hook 130 may be provided for ease of application.

The article of the present invention may have a plurality of elastic bodies disposed on each of the zones for providing the tensile stress. The elastic bodies disposed on the front proximal tummy zone 106 may have a density of no less than 540 dtex. The elastic bodies on the front proximal tummy zone 106 may be disposed at an elongation of at least 250%. In one embodiment, from 6 to 18 elastic bodies may be disposed on the front proximal tummy zone 106.

The elastic profiling described herein may be utilized for economically making an article of no less than 350 mm, or no less than 450 mm, or no less than 500 mm in the longitudinal axis by using a total of no more than 60, or no more than 46 elastic bodies for the elastic belt 40 per article.

The article of the present invention may have a Waist Circumference Force provided by the elastic bodies 96 disposed on the waist belt 40 of no more than 10N, or no more than 8N, according to the Whole Article Force Measurement as described herein below. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

In one embodiment, the elongation of the elastic bodies disposed on the front and back of the same zone are substantially matched. When a certain length of the elastic body is removed of its elasticity, the effective length of elasticity of such elastic body is considered. By matching the elongation rate of the elastic bodies disposed on the front and back of the same zone, and having the front and back belt 84, 86 have the same width LW, the article 20 may be manufactured such that in the unstretched, contracted condition, the article 20 can be flattened. The aforementioned shaping effect of the article 20 conforming to the wearer's body shape is exerted only when the article 20 is in the stretched, wearable condition. Such flattening capability is found for many commercially available pant-type wearable articles, and provides many benefits for providing the article economically. The capability of being flattened accommodates assembling, transferring, and packaging of the article 20.

The obtained wearable article of the present invention may provide fit, coverage of buttock area, comfort during wear, prevention of sagging, and prevention of leakage. The obtained wearable article of the present invention may be made in an economical manner.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 12:
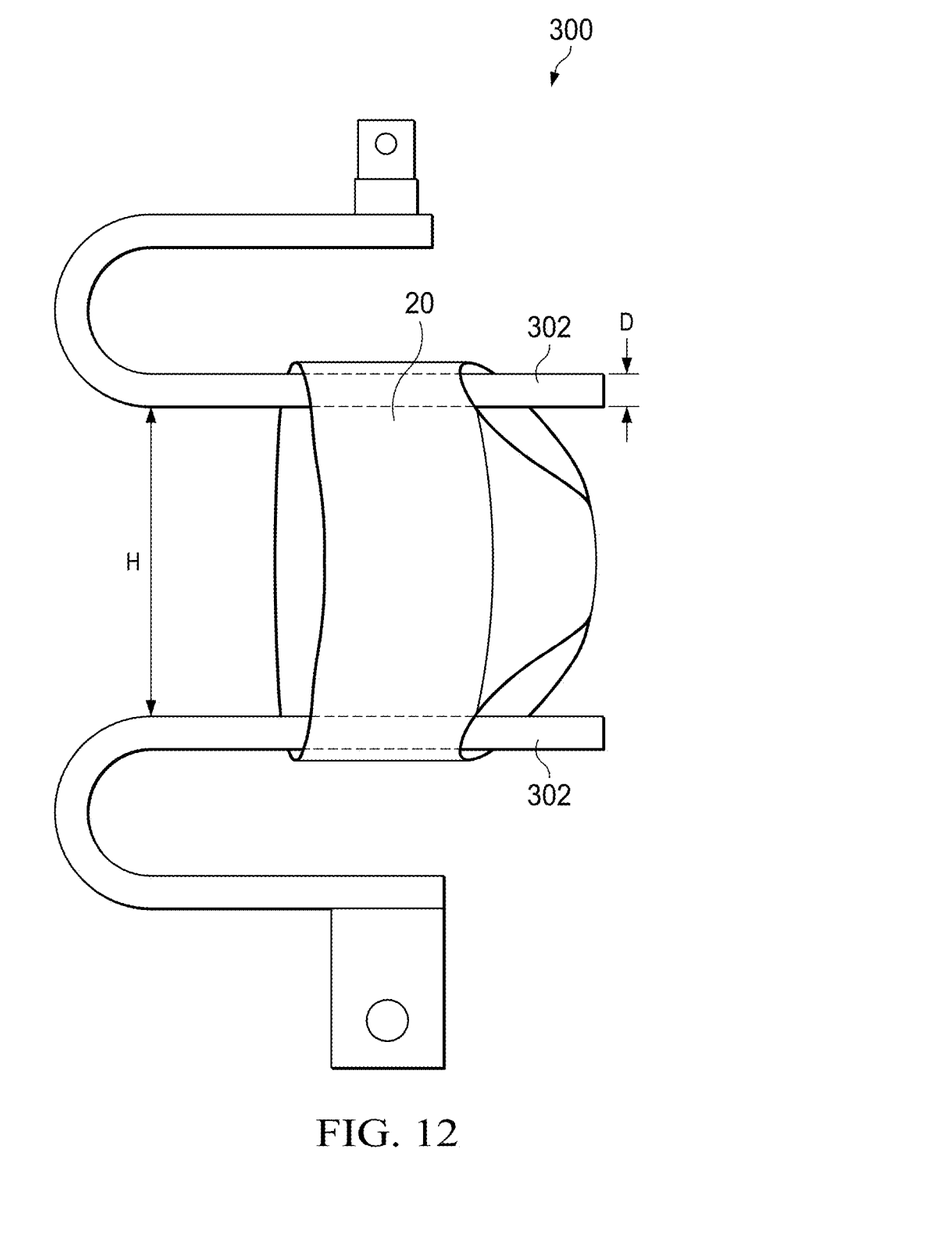
FIG. 12 is a schematic view of an example of a hanger-type sample holding fixture according to the "Whole Article Force Measurement".

The tensile tester is fitted with hanger-type sample holding fixtures 300 as shown in FIG. 12. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the initial gauge circumference at the same speed. The maximum circumference at 19.6N and the force at 70% stretch circumference during the extension segment of the test are recorded.

$$\text{Circumference (mm)} = 2 \times (H + D + \pi/2)$$

The maximum circumference at 19.6N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

Belt Zone Tensile Stress Measurement

The tensile stress (N/m) is calculated by tensile force (N) divided by the specimen width (m). Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is cut open along the side seams 32, and the front and rear elastic belt sections 40 are removed from the main body 38 by separating the bonding between the waist belt and main body. Cold Spray may be used, paying attention not to make wrinkles in the belt sections. Care is taken not to spray on any belt elastic body 96. The obtained elastic belts 40 are severed into zones 102, 104, 106, 108 according to the present invention with care not to cut any elastic body 96. Samples are pre-conditioned at 23° C.±2 C.° and 50%±5% relative humidity for two hours prior to testing.

The instrument is set up to go through the following steps. Initial Gauge Length is calculated from the Initial Gauge Circumference which is determined during the Whole Article Force Test using separate identical articles, as described above. Initial Gauge Length=0.5×Initial Gauge Circumference. The final gauge length is calculated from the Full Stretch Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × Full Stretch Circumference |
| Hold Time | 0 |
| Number of Cycles | 1 |

One end of the specimen is clamped into the upper clamp and the load is tared. The other end of the specimen is clamped into the lower clamp. Approximately 5 mm of each end of the specimen is behind the contact line of the grip. The test is started and the specimen is extended to the final gauge length at a crosshead speed of 254 mm/min, then immediately returned to the original gauge length at the same speed. The specimen is extended in the article transverse direction during the test. The unload force at 70% of the Final Gauge Length during the unload segments of the test is recorded.

Five articles are analyzed and the unload forces are recorded for each of the front and back zones 102, 104, 106, 108. The average tensile force (N) is calculated to the nearest 0.01 N for each zone including the front and back specimens for that zone. The tensile stress for each zone is calculated by the average tensile force (N) divided by the average specimen width (m) and reported to the nearest 0.1 N/m.

EXAMPLES

Examples 1-4

Wearable articles of the present invention having an elastic profiling according to FIGS. 2, 6, 8, 9, and Table 1 below, respectively, having a belt width LW of 355 mm and a seam length LS of 130 mm.

Comparative Example

Figure 11:
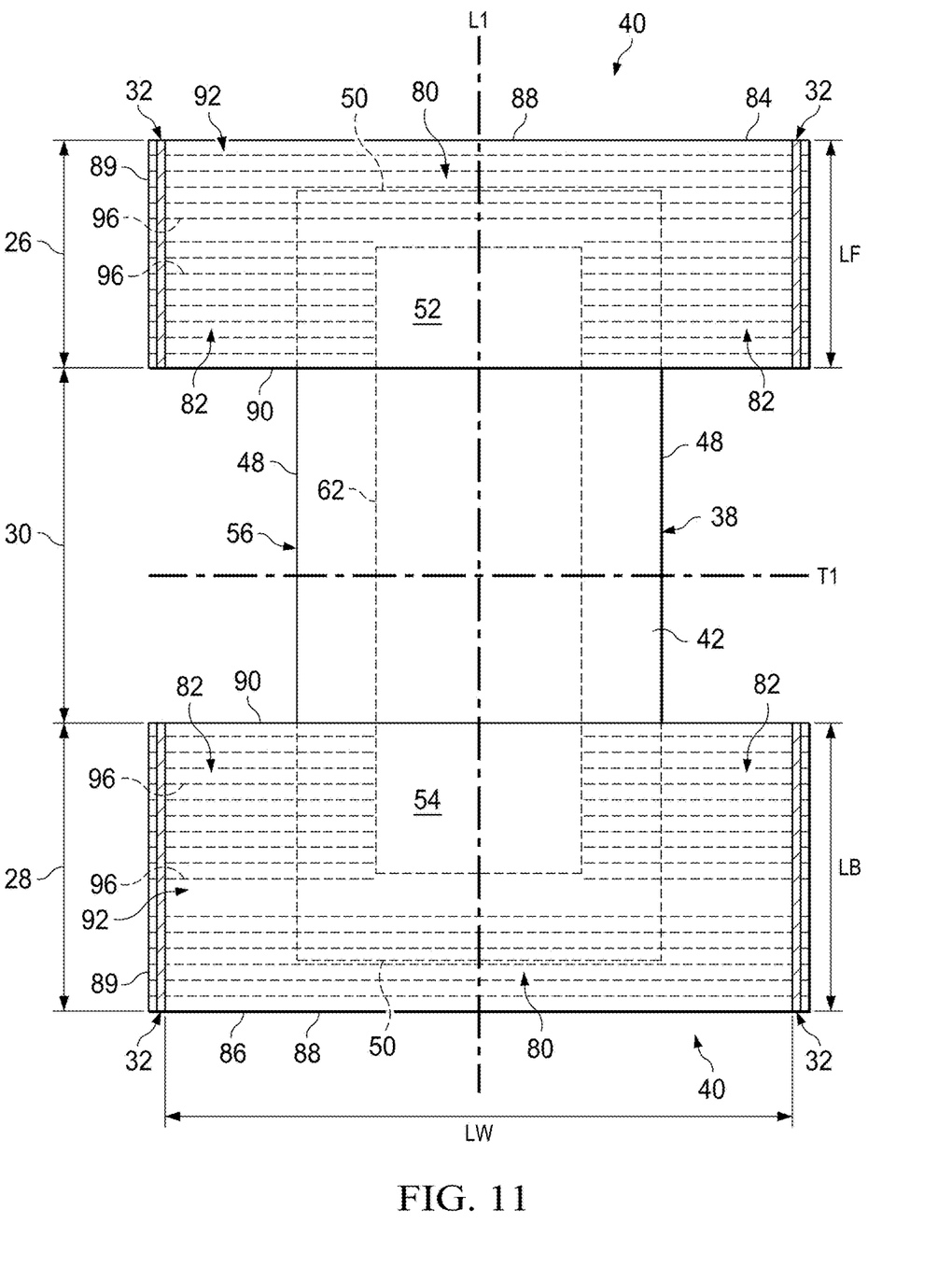
FIG. 11 is a schematic plan view of one embodiment of a wearable article of the prior art with the seams enjoined and in a flat uncontracted condition showing the garment facing surface.

A wearable article of the prior art having an elastic profiling according to FIG. 11 and Table 1 below having a belt width LW of 355 mm and a seam length LS of 130 mm.

Compared to the Comparative Example, Example 1 provides good buttock coverage, ease of application, and prevents red marking, sagging, and leakage. Compared to the Comparative Example, Examples 2 and 3 provides good shaping and fit. Compared to the Comparative Example, Example 4 provides good shaping, fit and comfort, and prevents red marking.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

TABLE 1

| Example | Comparative Example | Example 1 (FIG. 2) | Example 2 (FIG. 6) | Example 3 (FIG. 8) | Example 4 (FIG. 9) |
|---|---|---|---|---|---|
| Front waist zone (dtex/prestretch/#of elastics/cut window) | 940 dtex/210%/3/ 0 mm | 940 dtex/210%/3/ 0 mm | 680 dtex/275%/4/ 120 mm | 940 dtex/210%/4/ 0 mm | 540 dtex/170%/4/ 0 mm |
| Front distal tummy zone (dtex/prestretch/#of elastics/cut window) | 940 dtex/210%/3/ 0 mm | 940 dtex/210%/3/ 0 mm | 680 dtex/275%/4/ 110 mm | 680 dtex/275%/3/ 120 mm | 540 dtex/170%/2/ 0 mm |

TABLE 1-continued

| Example | Comparative Example | Example 1 (FIG. 2) | Example 2 (FIG. 6) | Example 3 (FIG. 8) | Example 4 (FIG. 9) |
|---|---|---|---|---|---|
| | 680 dtex/275%/1/ 120 mm | 680 dtex/275%/1/ 120 mm | | | 540 dtex/275%/2/ 120 mm |
| Front proximal tummy zone (dtex/prestretch/#of elastics/cut window) | 680 dtex/275%/5/ 120 mm | 680 dtex/275%/5/ 120 mm | 680 dtex/275%/1/ 100 mm 680 dtex/275%/1/ 80 mm 680 dtex/275%/4/ 0 mm | 680 dtex/275%/2/ 120 mm 680 dtex/275%/4/ 20 mm | 540 dtex/275%/2/ 80 mm 940 dtex/275%/6/ 80 mm |
| Front leg zone (dtex/prestretch/#of elastics/cut window) | 680 dtex/275%/2/ 120 mm | 680 dtex/275%/2/ 120 mm | 680 dtex/275%/2/ 120 mm | 680 dtex/275%/2/ 120 mm | 540 dtex/275%/2/ 120 mm |
| Back waist zone (dtex/prestretch %/# of elastics) | 940 dtex/210%/3 | 940 dtex/210%/3 | 680 dtex/275%/4 | 940 dtex/210%/4 | 540 dtex/170%/4 |
| Back distal tummy zone (dtex/prestretch/#of elastics/cut window) | 1100 dtex/170%/ 3/0 mm | 1100 dtex/170%/ 3/0 mm | 1100 dtex/170%/ 4/0 mm | 1100 dtex/170%/ 4/0 mm | 940 dtex/170%/4/ 0 mm |
| Back proximal tummy zone (dtex/prestretch/#of elastics/cut window) | 680 dtex/275%/4/ 120 mm | 680 dtex/275%/4/ 180 mm | 680 dtex/275%/2/ 100 mm 680 dtex/275%/4/ 130 mm | 680 dtex/275%/2/ 100 mm 680 dtex/275%/4/ 130 mm | 540 dtex/275%/4/ 120 mm 540 dtex/275%/2/ 180 mm |
| Back leg zone (dtex/prestretch/#of elastics/cut window) | 680 dtex/275%/3/ 120 mm | 680 dtex/275%/3/ 180 mm | 680 dtex/275%/4/ 180 mm | 680 dtex/275%/4/ 180 mm | 540 dtex/275%/2/ 180 mm |
| Buttock cover (dtex/prestretch/#of elastics/cut window) | 680 dtex/232%/ 2/120 mm 1100 dtex/232%/ 1/120 mm | 680 dtex/232%/ 2/180 mm 1100 dtex/232%/ 1/180 mm | 680 dtex/232%/ 2/200 mm 1100 dtex/232%/ 1/200 mm | 680 dtex/232%/ 2/180 mm 1100 dtex/232%/ 1/180 mm | 680 dtex/232%/ 1/180 mm 1100 dtex/232%/ 1/180 mm |

What is claimed is:

1. A wearable article, comprising:
a main body;
a front belt;
a back belt;
wherein a center of the front belt is joined to a front waist panel of the main body;
wherein a center of the back belt is joined to a back waist panel of the main body;
wherein the front and back belts each have a left side panel and a right side panel where the main body does not overlap, and transverse edges of the front belt and the back belt are joined by side seams to form a waist opening and two leg openings;
wherein each of the front belt and back belt are formed by an inner sheet, an outer sheet, and a plurality of elastic bodies sandwiched therebetween and running in the transverse direction substantially parallel to each other, and at least a portion of elasticity of at least some of the elastic bodies is removed of its elasticity, such that a transverse width of an elastic body removed of its elasticity defines an elastic cut window;
wherein the front belt has a set of elastic cut windows, and wherein the transverse width of the elastic body having a longest length removed of its elasticity defined as a maximum elastic cut window of the front belt;
wherein the back belt has a set of elastic cut windows, and wherein the transverse width of the elastic body having a longest length removed of its elasticity defined as a maximum elastic cut window of the back belt;
wherein the maximum elastic cut window of the back belt is greater than the maximum elastic cut window of the front belt;
wherein each front belt and back belt have transversely continuous proximal and distal edges, the proximal edge being located closer than the distal edge relative to a longitudinal center of the article, each front belt and back belt having side edges;
wherein an entirety of the length of the belt side edge of the front belt is seamed with a certain length of the belt side edge of the back belt to define a side seam length LS;
wherein the front and back belts are each divided into 4 zones extending in the transverse direction and defined by its location from the distal edge to the proximal edge relative to the percentage of the side seam length LS wherein 0-25% is defined a waist zone, 25-50% is defined a distal tummy zone, 50-85% is defined a proximal tummy zone, and 85-100% is defined a leg zone.

2. The article of claim 1 wherein at least one of the front belt or the back belt comprises varied elastic cut windows within the set of elastic cut windows.

3. The article of claim 2 wherein the front belt and the back belt each comprises varied elastic cut windows within the set of elastic cut windows.

4. The article of claim 1 wherein the back belt comprises elastic cut windows in at least the proximal tummy zone and the leg zone, and the elastic cut windows of the leg zone are greater than the elastic cut windows of the proximal tummy zone.

5. The article of claim 4 wherein the back belt further comprises elastic cut windows in the distal tummy zone, and the elastic cut windows of the proximal tummy zone are greater than the elastic cut windows of the distal tummy zone.

6. The article of claim 1 wherein a tensile stress of the back belt is in a relationship of: distal tummy zone>proximal tummy zone>leg zone.

7. The article of claim 1 wherein the maximum elastic cut window of the front belt is disposed on the distal tummy zone.

8. The article of claim 1 wherein the maximum elastic cut window of the front belt is disposed on the leg zone.

9. The article of claim 1 wherein the elastic cut windows of the elastic bodies disposed on the front proximal tummy zone are smaller than the elastic cut windows of the elastic bodies disposed on the front distal tummy zone and the front leg zone.

10. The article of claim 1 wherein the elastic bodies disposed on the waist zone of the front belt has an elastic cut window.

11. The article of claim 1 wherein the main body comprises a liquid permeable topsheet, a liquid impermeable backsheet, and an absorbent core disposed between the topsheet and the backsheet, wherein the maximum elastic cut window of the back belt is greater than a width of the absorbent core.

12. The article of claim 11 wherein the main body comprises a pair of cuffs disposed along and extending from the longitudinal side edges of the main body, each cuff comprising a cuff elastic body at the distal edge of the cuff, the maximum elastic cut window of the back belt being greater than a lateral distance between the cuff elastic bodies.

13. The article of claim 11 wherein the maximum elastic cut window of the back belt is greater than a lateral distance of the main body.

14. The article of claim 11 wherein each of the proximal edges and the distal edges of the front belt and the back belt are substantially parallel, a longitudinal length of the back belt being longer than that of the front belt, wherein the distal edge of the front belt is aligned with the distal edge of the back belt, and the proximal edge of the front belt is not aligned with the proximal edge of the back belt, a proximal portion of the back belt beyond the proximal edge of the front belt is a buttock cover zone.

15. The article of claim 14 wherein the maximum elastic cut window of the back belt is disposed on the buttock cover zone.

16. The article of claim 11 wherein the main body comprises a substantially cellulose free absorbent core including first and second absorbent layers, the first absorbent layer including a first substrate and the second absorbent layer including a second substrate, the first and second absorbent layers further including superabsorbent particulate polymer material deposited on said first and second substrates and thermoplastic adhesive material covering the absorbent particulate polymer material on the respective first and second substrates, said first and second absorbent layers combined together such that at least a portion of said thermoplastic adhesive material of said first absorbent layer contacts at least a portion of the thermoplastic adhesive material of said second absorbent layer, the absorbent particulate polymer material is disposed between the first and second substrates in an absorbent particulate polymer material area, and the absorbent particulate polymer material is substantially continuously distributed across the absorbent particulate polymer material area.

17. The article of claim 16 wherein the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such that the respective patterns of absorbent particulate polymer material are offset from one another.

18. The article of claim 1 wherein the elastic belt is disposed of a total of no more than 60 elastic bodies.

19. The article of claim 1 wherein a Waist Circumference Force according to a Whole Article Force Measurement disclosed herein is no more than 10N.

* * * * *